United States Patent [19]

Bazile et al.

[11] Patent Number: 5,856,435

[45] Date of Patent: *Jan. 5, 1999

[54] NUCLEIC ACID-CONTAINING COMPOSITION, ITS PREPARATION AND USE

[75] Inventors: Didier Bazile, Saint Maur Des Fosses; Carole Emile; Claude Helene, both of Paris; Gilles Spenlehauer, Cachan, all of France

[73] Assignee: Rhone-Poulenc Rorer SA, Anthony Cedex, France

[ * ] Notice: This patent issued on a continued prosecution application filed under 37 CFR 1.53(d), and is subject to the twenty year patent term provisions of 35 U.S.C. 154(a)(2).

[21] Appl. No.: 687,551

[22] PCT Filed: Jan. 27, 1995

[86] PCT No.: PCT/FR95/00098

§ 371 Date: Aug. 26, 1996

§ 102(e) Date: Aug. 26, 1996

[87] PCT Pub. No.: WO95/21931

PCT Pub. Date: Aug. 17, 1995

[30] Foreign Application Priority Data

Feb. 8, 1994 [FR] France .................................. 94 01381

[51] Int. Cl.[6] .............................. C07K 5/00; C07H 21/04; C12Q 1/68; C12N 15/85
[52] U.S. Cl. ........................ 530/300; 536/23.1; 536/24.5; 435/6; 435/69.1; 435/325
[58] Field of Search .................................. 514/44, 12, 13, 514/14, 15, 16, 17, 18; 536/23.1, 24.5; 530/300; 435/6, 69.1

[56] References Cited

U.S. PATENT DOCUMENTS

| | | | |
|---|---|---|---|
| 5,187,260 | 2/1993 | Karali et al. | 530/358 |
| 5,354,844 | 10/1994 | Beug et al. | 530/345 |
| 5,585,479 | 12/1996 | Hoke et al. | 536/24.5 |
| 5,670,347 | 9/1997 | Gopal . | |

OTHER PUBLICATIONS

Mulligan, The basic science of gene therapy, Science, vol. 260, pp. 926–932, May 1993.

Uhlmann et al., Antisense oligonucleotides: a new therapeutic principle, Chemical Reviews, vol. 90(4), pp. 543–584, Jun. 1990.

Weiss, Upping the antisense ante, scientist bet on profits from reverse genetics, Science News, vol. 139, pp. 108–109, Feb. 1991.

Tseng et al., Antisense oligonucleotide technology in the development of cancer therapeutics, Cancer Gene Therapy, vol. 1(1), pp. 65–71, Mar. 1994.

Gewirtz et al., Facilitating oligonucleotide delivery: helping antisense deliver on its promise, Proc. Natl. Acad. Sci., vol. 93, pp. 3161–3163, Apr. 1996.

Zhou et al., Lipophilic polylysines mediate efficient DNA transfection in mammalian cells, Biochim. Biophys. Acta., vol. 1065, pp. 8–14, 1991.

Barbier et al., Conformation–controlled hydrolysis of polyribonucleotides by sequential basic polypeptides, J. Am. Chem. Soc., vol. 114, pp. 3511–3515, 1992.

*Primary Examiner*—David Guzo
*Assistant Examiner*—Andrew Wang
*Attorney, Agent, or Firm*—Christine M. Hansen

[57] ABSTRACT

The present invention relates to compositions comprising nucleic acids and oligopeptides, and their use in therapy and in gene therapy, in particular for the transfer of nucleic acids.

21 Claims, No Drawings

NUCLEIC ACID-CONTAINING COMPOSITION, ITS PREPARATION AND USE

This application is a 371 of PCT/FR95/00098, filed Jan. 27, 1995.

The present invention relates to compositions based on nucleic acids, to their preparation and to their use. More especially, it relates to compositions comprising nucleic acids and oligopeptides and their use in gene therapy, in particular for the transfer of nucleic acids.

Gene therapy consists in correcting a deficiency or an abnormality (mutation, aberrant expression, and the like) by introducing genetic information into the cell or organic affected. This genetic information may be introduced either in vitro into a cell extracted from the organ, the modified cell then being reintroduced into the body, or directly in vivo into the appropriate tissue. Different techniques have been described for the transfer of this genetic information, including various techniques of transfection involving complexes of DNA and DEAE-dextran (Pagano et al., J. Virol. 1 (1967) 891), of DNA and nuclear proteins (Kaneda et al., Science 243 (1989) 375), and of DNA and lipids (Felgner et al., PNAS 84 (1987) 7413), the use of liposomes (Fraley et al., J. Biol. Chem. 255 (1980) 10431), and the like. More recently, the use of viruses as vectors for gene transfer has been seen to be a promising alternative to these physical transfection techniques. In this connection, different viruses have been tested for their capacity to infect certain cell populations. This applies especially to retroviruses (RSV, HMS, MMS, and the like), the HSV virus, adeno-associated viruses and adenoviruses.

However, the techniques developed hitherto do not enable the difficulties associated with the transfer of genes into cells and/or the body to be solved satisfactorily. In particular, the problems associated with the entry of the nucleic acid into the cells have not been solved completely. In effect, the polyanionic nature of nucleic acids prevents them from passing through the cell membranes. While it has been shown that naked nucleic acids are capable of passing through the plasma membrane ex vivo (see, in particular, Application No. WO90/11092), the efficiency of transfection remains fairly low. Furthermore, naked nucleic acids have a short plasma half-time on account of their degradation by enzymes and their elimination via the urine. Moreover, while recombinant viruses enable the efficiency of transfer of nucleic acids to be improved, their use incurs some risks, such as pathogenicity, transmission, replication, recombination, transformation, and the like.

The present invention provides an advantageous solution to these different problems. The Applicant has, in effect, shown that it is possible to form pairs of ions between particular cationic oligopeptides and the phosphate groups of nucleic acids, and that the complexes thus formed are stable and are capable of entering cells or of being encapsulated in transfer vectors such as liposomes, nanoparticles or low density lipoproteins (LDL), with high yields.

Hence a first subject of the invention lies in a composition comprising a nucleic acid and a cationic oligopeptide capable of forming secondary structures. The term secondary structure denotes peptides capable of adopting a particular spatial conformation under physiological conditions, as opposed to peptides not displaying any particular organization of their primary structure. The secondary structure may arise either in some solvents, or in aqueous solution, or after complexing with the nucleic acid.

More especially, the oligopeptides used in the context of the invention are capable of forming α helices or β sheets.

The complexing of a nucleic acid with a polylysine has already been described in the prior art. However, the degree of complexing and the stability of the complex formed with polylysine are relatively low, and these complexes cannot be encapsulated satisfactorily in transfer vectors (see Examples). In contrast, the complexes according to the invention, which involve cationic oligopeptides capable of forming secondary structures (αhelices, β sheets), display high stability, may be obtained with yields close to 100% and are capable of being encapsulated in transfer vectors with high yields. These complexes hence constitute especially advantageous tools for the transfer of nucleic acids into cells. Moreover, depending on the nature of the transfer vector used, the compositions of the invention may be used on cells extracted from the body (ex vivo) with a view to their re-administration, or directly in vivo.

More especially, the oligopeptides used in the context of the present invention correspond to the formula $(A_oA_yA_yA_o)n$ (SEQ ID NO:1) or $(A_oA_yA_oA_y)n$ (SEQ ID NO:2) in which $A_o$ is a hydrophobic amino acid, $A_y$ is a hydrophilic amino acid and n is an integer greater than or equal to 4. The Applicant has, in effect, shown that such oligopeptides are capable, when complexed with nucleic acids, of forming secondary structures which strongly stabilize the said complexes.

More preferably, the hydrophobic amino acid is chosen from leucine, valine, isoleucine and phenylalanine; and the hydrophilic amino acid is chosen from lysine, arginine and histidine.

The capacity of the oligopeptides to form secondary structures may be verified by circular dichroism or in NMR, as shown in the examples.

Still more preferably, the oligopeptide according to the invention is chosen from the oligopeptides of formula (LKKL)n (SEQ ID NO:3), (LKLK)n (SEQ ID NO:4) or (LRRL)n (SEQ ID NO:5), in which n is defined as above.

Generally speaking, in the oligopeptides of the invention, n can vary between 4 and 100, and preferably between 10 and 50. The value of n is adapted by a person skilled in the art in accordance with the length and nature of the nucleic acid, the composition of the oligopeptide, the desired use, and the like.

In order to obtain an optimum effect of the compositions of the invention, the respective proportions of the oligopeptide and of the nucleic acid are preferably determined in such a way that the ratio of positive charges of the oligopeptide to negative charges of the nucleic acid is equal to or greater than 1 (this ratio is designated R in the Examples). Thus, the longer the nucleic acid, the higher the number of positive charges supplied by the oligopeptide has to be in order to obtain a maximum effect. This can result either in the use of oligopeptides in which the value of n is higher, or in the use of larger amounts of oligopeptides, or alternatively in both.

The oligopeptides used in the context of the present invention may be prepared by any technique known to a person skilled in the art. Preferably, they are synthesized chemically by means of a peptide synthesizer, using any type of chemistry known to a person skilled in the art (F-moc, T-boc, and the like). When the values of n are high, it is, moreover, possible to synthesize the oligopeptides in several fragments which are then assembled. Moreover, depending on the synthesis technique used (for example in a homogeneous phase), the oligopeptide obtained may be not a defined compound, but a mixture of oligopeptides having different lengths centered around a mean. In this case, the value of n in the formula of the invention represents the mean of the n values of the different constituents of the mixture. Suitable methods of synthesis are given in the general techniques of molecular biology and in the Examples.

For the purposes of the present invention, the term nucleic acid comprises both deoxyribonucleic acids and ribonucleic acids. The nucleic acid can comprise sequences of natural or artificial origin, and in particular genomic DNA, cDNA, mRNA, tRNA, rRNA, hybrid sequences or synthetic or semi-synthetic sequences. These nucleic acids may be of human, animal, vegetable, bacterial, viral, and the like, origin. They may be obtained by any technique known to a person skilled in the art, and in particular by the screening of libraries, by chemical synthesis or alternatively by mixed methods including the chemical or enzymatic modification of sequences obtained by the screening of libraries. They may, moreover, be incorporated in vectors such as plasmid vectors.

In the case of deoxyribonucleic acids more especially, the latter may be single- or double-stranded. These deoxyribonucleic acids may carry therapeutic genes, sequences that regulate transcription, antisense sequences, regions for binding to other cell components, and the like.

For the purposes of the invention, therapeutic gene is understood, in particular, to mean any gene coding for one or more proteins (or peptide or polypeptide) having pharmacological activity. Such encoded products can be enzymes, hormones, growth factors, lymphokines, apolipoproteins, and the like. Antisense sequence is understood to mean any sequence capable, directly or indirectly (after transcription into RNA), of reducing the levels of expression of a desired protein, or even of abolishing them (EP 140,038). The antisense sequences also comprise the sequences coding for ribozymes, which are capable of selectively destroying target RNAs (EP 321,201).

In the case of ribonucleic acids (RNAs) more especially, the latter may be antisense RNAs, capable of at least partially blocking the translation of target mRNAs (of cellular, viral, bacterial, and the like, origin); or they can also be ribozymes or nucleic acids capable of binding to another nucleic acid by formation of a triple helix.

The compositions according to the invention may be used in vitro, ex vivo or in vivo. In vitro, they can enable desired nucleic acid sequences to be transferred to cell lines, for example with the object of expressing a recombinant protein or an antisense activity, or with the object of inhibiting a protein by binding of the said protein to the nucleic acid. Ex vivo, they may be used for the therapeutic transfer of a nucleic acid into a cell originating from a body, for the purpose of endowing the said cell with new or strengthened properties before it is re-administered to a body. In vivo, they may be used for the direct administration of nucleic acid.

Another subject of the invention hence lies in the use of a cationic oligopeptide capable of forming secondary structures for the transfer of nucleic acids into cells. As mentioned above, this transfer may be performed in vitro, ex vivo or in vivo.

The compositions according to the invention can enable nucleic acids to be transferred into miscellaneous types of cells. The cells in question are preferably animal cells, preferably human. They can be, in particular, haematopoietic, endothelial, myoblastic, and the like, cells. They can, moreover, be either healthy cells or cells affected by dysfunctions (tumour, viral infection, and the like).

The invention also relates to a method for the transfer of a nucleic acid into a cell, characterized in that the said cell is cultured in the presence of the nucleic acid and a cationic oligopeptide capable of forming secondary structures.

Moreover, the nucleic acid-oligopeptide complexes of the present invention also enable nucleic acids to be encapsulated in transfer vectors with considerably improved yields. To decrease the problems of stability and of entry into cells, the nucleic acids may, in effect, be combined with suitable drug carriers or vectors. Encapsulation of nucleic acids in such transfer vectors makes it possible to protect them from serum nucleases, to facilitate their entry into the cells containing their pharmacological target and to slow down their elimination. However, the major difficulty limiting the use of these vectors lies in the low yields of encapsulation of the nucleic acids. The Applicant has now shown that the nucleic acid-oligopeptide complexes of the invention may be encapsulated in transfer vectors with high yields. More especially, the encapsulation yields of the complexes of the invention in nanoparticles are greater than 50%, whereas they are less than 1% with naked nucleic acids or with other oligopeptides that do not form secondary structure (see Examples).

Another subject of the invention hence lies in the use of a cationic oligopeptide capable of forming secondary structures for the encapsulation of nucleic acids in a transfer vector.

The subject of the invention is also the vectors for the transfer of nucleic acids comprising a composition as defined above.

Among the different transfer vectors, it is preferable to use, in the context of the present invention, biocompatible, biodegradable and hydrophobic vectors of a proteinaceous or polymeric nature. In particular, the preferred vectors according to the invention are liposomes, nanoparticles or low density lipoproteins (LDL).

Liposomes are phospholipid vesicles containing an internal aqueous phase in which nucleic acids may be encapsulated. The synthesis of liposomes and their use for the transfer of nucleic acids is known in the prior art (WO91/06309, WO92/19752, WO92/19730). The use of complexes according to the invention enables the efficiency of encapsulation of nucleic acids in liposomes to be improved.

Nanoparticles are small particles generally less than 500 nm in size, capable of transporting or conveying an active principle (such as a nucleic acid) in cells or in the blood stream. The present invention also enables the encapsulation yields of nucleic acids in nanoparticles to be improved considerably. Preferably, the nanoparticles according to the invention consist of polymers containing a majority of degradable motifs, such as polylactic acid, optionally copolymerized with polyethylene glycol. Other polymers which can be used in the production of nanoparticles have been described in the prior art (see, for example, EP 275,796; EP 520,889).

Hence the invention also relates to a method of encapsulation of nucleic acids in transfer vectors, according to which the transfer vector or the components of which it is made up, the nucleic acid and a cationic oligopeptide capable of forming secondary structures, or, where appropriate, an already formed nucleic acid-oligopeptide complex, are brought into contact under conditions permitting encapsulation of the nucleic acid in the said transfer vector, and the transfer vector formed is then recovered. As mentioned above, the method according to the invention is preferably applied for the preparation of liposomes, nanoparticles or low density lipoproteins.

The invention also relates to pharmaceutical compositions comprising a therapeutic nucleic acid and a cationic oligopeptide capable of forming secondary structures, where appropriate encapsulated in a transfer vector.

The present invention will be described more fully by means of the Examples which follow, which are to be considered to be illustrative and non-limiting.

EXAMPLE 1

Preparation of Oligopeptides

The following three oligopeptides were synthesized:

1.1. —(H)-(Leucine-Lysine-Lysine-Leucine)$_{10}$-(OH) or (LKKL)$_{10}$. (SEQ ID NO:6)

This oligopeptide was synthesized in the form of a trifluoroacetic acid salt by means of an Applied Biosystem 431A peptide synthesizer, on an HMP resin (Applied Biosystem) and according to an F-MOC strategy. After the synthesis, the peptide was liberated from the resin by treatment for 90 minutes in the presence of a 95:5 (v/v) TFA/water solution, precipitated by adding tert-butyl methyl ether and then purified by reversed-phase HPLC on a C18 100 A column (Biorad RSL). The purity of the peptide obtained is greater than 95% and its solubility in water is 50 mg/ml. It was shown that the polytetrapeptide LKKL (SEQ ID NO:3), unstructured in water, adopts an α-helical conformation in saline solution. This conformation should improve the stability of the complex by forming ion pairs between the positive charges of the lysines of the oligopeptide and the phosphates, ionized at physiological pH, of the nucleic acid.

1.2. —(H)-(Leucine-Lysine-Leucine-Lysine)$_{10}$-(OH) or (LKLK)$_{10}$. (SEQ ID NO:7)

This oligopeptide was synthesized in the form of a trifluoroacetic acid salt according to the protocol described above. The purity of the peptide obtained is greater than 90% and its solubility in water is 100 mg/ml. It was shown that the polytetrapeptide LKLK (SEQ ID NO:4), unstructured in water, adopts a β-sheet conformation in saline solution or in the presence of nucleic acids, as a result of the interaction between phosphates and amino groups. Along a β sheet, the distance separating two positive charges is 6.9 A, which is compatible with the 6.2 A separating two phosphate groups of a single-stranded nucleic acid. This conformation should hence improve the stability of the complex.

1.3. —(H)-(Proline-Lysine-Lysine-Leucine)$_{10}$-(OH) or (PKKL)$_{10}$. (SEQ ID NO:8)

This peptide, supplied by A. Brack, Molecular Biophysics Centre, Orléans) is not structured in saline solution and was used as a control.

1.4. Polylysine

The polylysine used is of commercial origin. This peptide is not structured in saline solution and was used as a control.

EXAMPLE 2

Nucleic Acids Used 2.1. Anti-ras Val12 antisense nucleic acids

Anti-ras antisense nucleic acids were prepared. These nucleic acids are oligonucleotides of 12 and 13 residues, synthesized by the company Eurogentec (Belgium). These oligonucleotides are directed against a sequence of ras mRNA mutated in the twelfth codon. The nucleic acids used are the antisense sequence (AS-Val), its inverse (INV-Val: the sequence is identical but oriented in the opposite direction), as well as the antisense sequence of normal ras mRNA (AS-Gly) and a control nucleic acid containing 2 unpaired nucleotides in the middle of the sequence (AS-mut2). The sequences of these nucleic acids is as follows:

| | |
|---|---|
| 3'-CGCGGCAGCCAC-5' | (AS-Val12) (SEQ ID NO: 9) |
| 3'-GCGGCAGCCACAC-5' | (AS-Val13) (SEQ ID NO: 10) |
| 3'-CACCGACGGCGC-5' | (INV-Val12) (SEQ ID NO: 11) |
| 3'-CACACCGACGGCG-5' | (INV-Val13) (SEQ ID NO: 12) |
| 3'-CGCGGCCGCCAC-5' | (AS-Gly12) (SEQ ID NO: 13) |
| 3'-CGCCGGAGCCAC-5' | (AS-mut212) (SEQ ID NO: 14) |

2.2. Nucleic acid (d(Tp)15T)

The nucleic acid (d(Tp)15T) is composed of 16 thymidines (SEQ ID NO:15). It is of commercial origin (Pharmacia).

EXAMPLE 3

Study of Complexing

This example illustrates the formation of complexes between the antisense nucleic acids described in Example 2 and the oligopeptides described in Example 1, under different conditions of ionic strength and concentration (all the nucleic acid concentrations are expressed as phosphate). It shows that very high complexing yields may be obtained, thus testifying to the stability of the complexes.

3.1. Complexing in phosphate buffer

The nucleic acid ($10^{-4}$M expressed as phosphate: $C_{phosphate} = 12 \times C_{nucleic\ acid}$) and the oligopeptide (concentration varying between $2 \times 10^{-3}$, $10^{-4}$ and $2 \times 10^{-5}$ expressed as positive charges) were brought into contact in 50 mM phosphate buffer pH 7.4. The solution was then centrifuged, and the absorbance (A) at 256 nm (absorption maximum of nucleic acids) was determined in the supernatant. For each value of the ratio R (number of positive charges of the oligopeptide/number of negative charges of the nucleic acid) tested, the value A/A0 is determined, enabling the free nucleic acid fraction to be evaluated and, by difference, the fraction complexed. For a ratio R=1, the oligopeptide concentration expressed as lysine is hence $10^{-4}$M.

The results obtained show that the fraction of complex precipitating AS-Val13/LKKL$_{10}$ (SEQ ID NO:6) or INV-Val13/LKKL$_{10}$ (SEQ ID NO:6) is 85% for a ratio R=2. For a ratio R=1, the fraction of complex precipitating AS-Val13/LKLK10 (SEQ ID NO:7) and INV-Val13/LKLK10 (SEQ ID NO:7) is lower: 30%. These results may be explained by a competition between the phosphates of the buffer and the phosphates of the nucleic acid for the formation of the complex. These results are, however, superior to those obtained with the control oligopeptide: only 15% of complex INV-Val13/PKKL10 (SEQ ID NO:8) precipitating.

3.2. Complexing in Tris-HCl buffer

The nucleic acid ($10^{-4}$M) and the oligopeptide (variable concentration) were brought into contact in 50 mM Tris-HCl buffer pH 7.4. The solution was then centrifuged and the absorbance at 256 nm was determined in the supernatant. For each value of the ratio R tested, the value A/A0 is determined as above.

The results obtained show that the fraction of complex precipitating AS-Val13/LKKL10 (SEQ ID NO:6) and AS-Val13/LKLK10 (SEQ ID NO:7) is 100% for a ratio R=1. For a ratio R=2, the fraction of complex precipitating AS-Val13/LKLK10 (SEQ ID NO:7) is also 100%. Moreover, 100% of complex precipitating AS-Val13/LKKL10 (SEQ ID NO:6) was also obtained with a nucleic acid concentration of $2 \times 10^{-5}$M and a ratio R=1.

In contrast, as regards the complex AS-Val13/PKKL10 (SEQ ID NO:8), only 70% of the nucleic acids involved in the complex precipitates, thereby demonstrating that the affinity of the oligopeptides according to the invention is greater.

3.3. Complexing in water

The above protocol was repeated, replacing Tris-HCl buffer by water. The same results were obtained (100% complexing for R=1), demonstrating the high affinity of the oligopeptides of the invention for the nucleic acids.

3.4. Conclusions

These results collectively demonstrate the high complexing yield of the oligopeptides of the invention with nucleic acids, and the fact that this yield is independent of the sequence and of the concentration of the nucleic acid used. Moreover, as shown in the Table below, a study of the dichroic spectra enabled the secondary structures adopted by the cationic oligopeptides used, in solution or after complexing, to be confirmed.

| Peptide | 50 mM phosphate buffer | 50 mM phosphate buffer/0.2 M NaCl | Water | Water/nucleic acid |
|---|---|---|---|---|
| LKKL | α Helix | α Helix | unstructured | α Helix |
| LKLK | β Sheet | β Sheet | unstructured | β Sheet |
| PKKL | unstructured | unstructured | unstructured | unstructured |

EXAMPLE 4

Study of Encapsulation in a Transfer Vector: Nanoparticles

This example illustrates the very advantageous properties of the complexes of the invention, enabling nucleic acid to be encapsulated in transfer vectors with very high yields.

4.1. Nanoparticles used:

The nanoparticles used in this example are diblock copolymers consisting of a poly(D,L-lactic acid) linked via an ester bond to a poly(ethylene glycol): PLAp(M)-PEG(N) where M and N are, respectively, the average molecular masses (in kD) of the PLA and the PEG, and p is the percentage of L-lactic acid. The 2 types of nanoparticles used are PLA50(30)-PEG(2) and PLA50(30)-PEG(5). These copolymers may be synthesized by any technique known to a person skilled in the art (see, for example, EP 520,889).

4.2. Radioactive labelling of the nucleic acids:

The nucleic acids were treated with phage T4 polynucleotide kinase (Biolabs) in the presence of $[\gamma-^{32}P]ATP$ (Amersham) in a kinase buffer. After 30 min of incubation at 37° C., the nucleic acid was separated from unreacted ATP by application to a Séphadex G25 column (Quick Spin) and centrifugation.

4.3. Encapsulation of the nucleic acid INV-Val13

This Example describes the encapsulation of the nucleic acid INV-Val13 in a nanoparticle of $PLA_{50}(30)$-PEG(2) in the presence or absence of oligopeptide $(LKKL)_{10}$(SEQ ID NO:6).

The polymer used, (PLA50(30)-PEG(2)), was solubilized in 1 ml of acetone at a concentration of 10 g/l. The isotopic dilution of the nucleic acid (final concentration $10^{-5}$M) was added, followed by the oligopeptide (at a concentration such that R=1). The organic solution obtained was then poured dropwise into 5 ml of an aqueous solution (50 mM Tris-HCl buffer pH 7.4) with stirring. The polymer, insoluble in the water/acetone mixture, precipitates in the form of nanoparticles, trapping the nucleic acid-oligopeptide complex. The acetone was then removed by evaporation under a partial vacuum, to a final volume of 2.5 ml. Lastly, the suspension of nanoparticles was filtered through a Sartorius filter of porosity 1.2 μm, which acts as a screen for dispersion and injectability.

A control experiment was performed under the same conditions but in the absence of the oligopeptide $(LKKL)_{10}$ (SEQ ID NO:6).

The results obtained show that the encapsulation yield of INV-Val13 in the nanoparticle is 56% in the presence of the oligopeptide, and only 5% without the oligopeptide.

The encapsulation yield corresponds to the percentage of nucleic acid encapsulated in the nanoparticles, relative to the total amount of nucleic acid present at the start.

4.4. Encapsulation of nucleic acid (d(Tp)15T) (SEQ ID NO:15)

The encapsulation yield of the nucleic acid (d(Tp)15T) (SEQ ID NO:15) (Example 2.2) in a nanoparticle of $PLA_{50}$ was studied, in the presence of the following cationic oligopeptides:

LKKLn (SEQ ID NO:3) α Helix: synthesized in a homogeneous phase in the form of a mixture of peptides of average molecular weight 34900.

LKLKn (SEQ ID NO:4) β Sheet: synthesized in a homogeneous phase in the form of a mixture of peptides of average molecular weight 7400.

PKKLn (SEQ ID NO:16) No secondary structure

Kn No secondary structure or of sphingosine (positively charged membrane lipid).

For this purpose, the nucleic acid (d(Tp)15T) (SEQ ID NO:15) was mixed with the oligopeptide dissolved in water. In the case of sphingosine, this is solubilized in a 50% v/v water/ethanol mixture. The concentrations used are shown in the Table below. 100 μl of a polylactic acid ($PLA_{50}$) solution solubilized in acetone at a concentration of 20 g/l were added to the mixture, as well as 300 μl of pure acetone (final $PLA_{50}$ concentration: 5 g/l). After homogenization by vortexing, the mixture was poured dropwise into a 2.5% (w/v) aqueous solution of pluronic F68 in order to precipitate the polymer in the form of a turbid colloidal suspension of nanoparticles. The turbidity was assessed by eye. The diameter of the nanoparticles (175+/−40 nm) was measured by quasi-elastic light scattering on a BI 90 apparatus (Brookhaven Instrument Corporation). The acetone was then evaporated off under vacuum for one hour. The suspension was then filtered through a millipore AP20 filter (pore diameter: 1.5 μm) previously wetted with the 2.5% pluronic F68 solution.

The encapsulation yield was determined and is recorded in the Table below.

| Peptide | (SEQ ID NO:3) LKKLn | (SEQ ID NO:4) LKLKn | (SEQ ID NO:16) PKKLn | Kn | Sphingo. |
|---|---|---|---|---|---|
| Structure | α Helix | β Sheet | none | none | one |
| Concentration of the peptide (mM) | 5 | 12.5 | 9.2 | 1 | 2.2 |
| Volume of peptide in the mixture (μl) | 11.4 | 65 | 48 | 60 | 27 |
| Amount of peptide (nmol) | 57 | 812 | 442 | 60 | 60 |
| Concentration of d (Tp) 15T | | | 71 μM | | |
| Volume of d (TP) 15T | | | 28 μl | | |
| Amount of d (Tp) 15T | | | 2 nmol | | |
| R | 2 | 27 | 14.7 | 2 | 2 |
| Yield | 42.8 | 7.8 | 0.8 | 0.3 | 1.3 |

These results show clearly that the oligopeptides of the invention enable nucleic acids to be encapsulated with yields markedly greater than those obtained with oligopeptides of the prior art (polylysine) or oligopeptides that do not form secondary structures (PKKL) (SEQ ID NO:16).

EXAMPLE 5

Transfer of Nucleic Acid Into Cells

This example illustrates the capacity of the composition of the invention to transfer nucleic acids into cells.

5.1. Cells used:

The tests of nucleic acid transfer described in this example were performed on a cell line originating from a human bladder carcinoma, designated T24/EJ, available in the ATCC. The cells were cultured in MEM-EAGLE medium ("minimum essential medium", Biological Industries) supplemented with L-glutamine ((5 mM), streptomycin (50 u/ml) and penicillin (50 u/ml) in the presence of 7% of foetal calf serum decomplemented for 30 min at 60° C.

5.2. Transfer of nucleic acids:

The cells (1500/well) were inoculated into 96-well microplates, in the absence or presence of nucleic acid, encapsulated or otherwise in nanoparticles, in a total volume of 100 μl. Each point was performed in triplicate. The concentration of nucleic acid used was adjusted by dilution in water or by concentration by centrifugation for 1 h at 12000 rpm. In this case, the suspension is centrifuged, the pellet is weighed and the volume is then adjusted.

The efficiency of transfer was determined by measuring the inhibition of cell proliferation induced by the antisense nucleic acid, after 72 or 96 hours of culture at 37° C. in the presence of 5% $CO_2$. For this purpose, 2 methods were used:

In the first place, the incorporation of tritiated thymidine, which was determined after adding 2 μCi of 3 H thymidine per well. After 6 hours of incubation in an incubator, the plates were washed with a Skatron apparatus (Lier, Norway), the DNA was collected on a filter and each disc of the filter (corresponding to each well of the plate) was placed in scintillation fluid and then counted in a counter (LKB Wallac 1211 Minibeta). The results correspond to the mean of the values obtained in each of the 3 wells.

Next, cell proliferation was evaluated by counting the cells in a Malassez cell. For this purpose, the supernatant was removed, the cells were trypsinized (10 min at 37° C.) and culture medium was added to them before they were counted.

The results obtained were as follows:

| | |
|---|---|
| AS-Val12, naked, 30 μM | 42% inhibition |
| AS-Val12/LKKL/nanoparticle, 100 nM (expressed as antisense) | 50% inhibition |
| Blank nanoparticle, same amount of polymer | <5% inhibition |
| AS-Val12/LKKL/nanoparticle, 500 nM | 95% inhibition |

These results clearly demonstrate the efficiency of the compositions of the invention for the transfer of nucleic acids. Furthermore, they show that the transferred nucleic acid retains its functional properties, in the present case its antisense activity.

---

We claim:

1. A composition comprising a deoxyribonucleic acid and a cationic oligopeptide that forms secondary structures, wherein the oligopeptide corresponds to the formula $(A_oA_yA_yA_o)n$ (SEQ ID NO:1) or $(A_oA_yA_oA_y)n$ (SEQ ID NO:2) in which $A_o$ is a hydrophobic amino acid, $A_y$ is a hydrophilic amino acid and n is an integer greater than or equal to 4.

2. The composition according to claim 1, characterized in that the oligopeptide forms α helices or β sheets.

3. The composition according to claim 1, characterized in that the hydrophobic amino acid is chosen from leucine, valine, isoleucine and phenylalanine.

4. The composition according to claim 1, characterized in that the hydrophilic amino acid is chosen from lysine, arginine and histidine.

5. The composition according to claim 1, characterized in that the oligopeptide is chosen from (LKKL)n (SEQ ID NO:3), (LKLK)n (SEQ ID NO:4) and (LRRL)n (SEQ ID NO:5).

6. The composition according to claim 5, characterized in that n is between 4 and 100.

7. The composition according to claim 1, characterized in that the deoxyribonucleic acid is chemically modified.

8. The composition according to claim 1, characterized in that the deoxyribonucleic acid is an antisense sequence.

9. The composition according to claim 1, characterized in that the deoxyribonucleic acid contains a therapeutic gene.

10. The composition according to claim 1, characterized in that the ratio of positive charges of the oligopeptide to negative charges of the deoxyribonucleic acid is greater than or equal to 1.

11. A vector for the transfer of deoxyribonucleic acids comprising a composition according to claim 1.

12. The vector of claim 11, characterized in that it is a nanoparticle, a liposome or a low density lipoprotein.

13. A method of encapsulation of deoxyribonucleic acids in transfer vectors, comprising:

(a) combining the transfer vector or its components and a composition according to claim 1 under conditions permitting encapsulation of the deoxyribonucleic acid in the transfer vector, and (b) recovering the transfer vector that is formed.

14. A method for the transfer of a deoxyribonucleic acid into a cell comprising the step of culturing the cell in the presence of the composition of claim 1.

15. A composition comprising a composition according to claim 1, and a pharmaceutically acceptable carrier.

16. A composition comprising a deoxyribonucleic acid and an oligopeptide of the formula (LKKL)n (SEQ ID NO:3), wherein the oligopeptide forms secondary structures and n is an integer greater than or equal to four.

17. A composition according to claim 16, characterized in that the deoxyribonucleic acid is an antisense sequence.

18. A method of encapsulation of deoxyribonucleic acids in transfer vectors, comprising:
   (a) combining the transfer vector or its components and a composition according to claim 16, and
   (b) recovering the transfer vector that is formed.

19. A vector for the transfer of deoxyribonucleic acids comprising a composition according to claim 17.

20. The vector of claim 19, characterized in that it is a nanoparticle, a liposome or a low density lipoprotein.

21. A method of transferring deoxyribonucleic acids into a cell, in vitro, comprising contacting the cell with a composition according to claim 16.

* * * * *

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 4 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Region
        ( B ) LOCATION: 1..4
        ( D ) OTHER INFORMATION: /note= "residues 1 and 4 are hydrophobic; residues 2 and 3 are hydrophilic"

( i x ) FEATURE:
        ( A ) NAME/KEY: Region
        ( B ) LOCATION: 1..4
        ( D ) OTHER INFORMATION: /note= "the sequence is repeated four or more times"

( x i ) SEQUENCE DESCRIPTION: SEQ ID NO:1:

Xaa  Xaa  Xaa  Xaa
    1

( 2 ) INFORMATION FOR SEQ ID NO:2:

( i ) SEQUENCE CHARACTERISTICS:
        ( A ) LENGTH: 4 amino acids (B) TYPE: amino acid
(C) STRANDEDNESS:
(D) TOPOLOGY: linear (ii) MOLECULE TYPE: peptide (ix) FEATURE:
(A) NAME/KEY: Region
(B) LOCATION: 1..4
(D) OTHER INFORMATION: /note= "residues 1 and 3 are hydrophobic; residues 2 and 4 are hydrophilic"

(ix) FEATURE:
(A) NAME/KEY: Region
(B) LOCATION: 1..4
(D) OTHER INFORMATION: /note= "the sequence is repeated four or more times"

(xi) SEQUENCE DESCRIPTION: SEQ ID NO:2:

Xaa Xaa Xaa Xaa
 1

(2) INFORMATION FOR SEQ ID NO:3:

(i) SEQUENCE CHARACTERISTICS:
(A) LENGTH: 4 amino acids
(B) TYPE: amino acid
(C) STRANDEDNESS:
(D) TOPOLOGY: linear (ii) MOLECULE TYPE: peptide (ix) FEATURE:
(A) NAME/KEY: Region
(B) LOCATION: 1..4
(D) OTHER INFORMATION: /note= "the sequence is repeated four or more times"

(xi) SEQUENCE DESCRIPTION: SEQ ID NO:3:

Leu Lys Lys Leu
 1

(2) INFORMATION FOR SEQ ID NO:4:

(i) SEQUENCE CHARACTERISTICS:
(A) LENGTH: 4 amino acids
(B) TYPE: amino acid
(C) STRANDEDNESS:
(D) TOPOLOGY: linear (ii) MOLECULE TYPE: peptide (ix) FEATURE:
(A) NAME/KEY: Region
(B) LOCATION: 1..4
(D) OTHER INFORMATION: /note= "the sequence is repeated four or more times"

(xi) SEQUENCE DESCRIPTION: SEQ ID NO:4:

Leu Lys Leu Lys
 1

(2) INFORMATION FOR SEQ ID NO:5:

(i) SEQUENCE CHARACTERISTICS:
(A) LENGTH: 4 amino acids
(B) TYPE: amino acid
(C) STRANDEDNESS:
(D) TOPOLOGY: linear (ii) MOLECULE TYPE: peptide (ix) FEATURE:
(A) NAME/KEY: Region (B) LOCATION: 1..4
        (D) OTHER INFORMATION: /note= "the sequence is repeated
            four or more times"

(xi) SEQUENCE DESCRIPTION: SEQ ID NO:5:

Leu  Arg  Arg  Leu
    1

(2) INFORMATION FOR SEQ ID NO:6:

(i) SEQUENCE CHARACTERISTICS:
        (A) LENGTH: 40 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:6:

Leu  Lys  Lys  Leu  Leu  Lys  Lys  Leu  Leu  Lys  Lys  Leu  Leu  Lys  Lys  Leu
    1                   5                        10                       15

Leu  Lys  Lys  Leu  Leu  Lys  Lys  Leu  Leu  Lys  Lys  Leu  Leu  Lys  Lys  Leu
                        20                       25                       30

Leu  Lys  Lys  Leu  Leu  Lys  Lys  Leu
                        35                       40

(2) INFORMATION FOR SEQ ID NO:7:

(i) SEQUENCE CHARACTERISTICS:
        (A) LENGTH: 40 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:7:

Leu  Lys  Leu  Lys  Leu  Lys  Leu  Lys  Leu  Lys  Leu  Lys  Leu  Lys  Leu  Lys
    1                   5                        10                       15

Leu  Lys  Leu  Lys  Leu  Lys  Leu  Lys  Leu  Lys  Leu  Lys  Leu  Lys  Leu  Lys
                        20                       25                       30

Leu  Lys  Leu  Lys  Leu  Lys  Leu  Lys
                        35                       40

(2) INFORMATION FOR SEQ ID NO:8:

(i) SEQUENCE CHARACTERISTICS:
        (A) LENGTH: 40 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:8:

Pro  Lys  Lys  Leu  Pro  Lys  Lys  Leu  Pro  Lys  Lys  Leu  Pro  Lys  Lys  Leu
    1                   5                        10                       15

Pro  Lys  Lys  Leu  Pro  Lys  Lys  Leu  Pro  Lys  Lys  Leu  Pro  Lys  Lys  Leu
                        20                       25                       30

Pro  Lys  Lys  Leu  Pro  Lys  Lys  Leu
                        35                       40

(2) INFORMATION FOR SEQ ID NO:9:

(i) SEQUENCE CHARACTERISTICS:
        (A) LENGTH: 12 base pairs ( B ) TYPE: nucleic acid
        ( C ) STRANDEDNESS: single
        ( D ) TOPOLOGY: linear ( i i ) MOLECULE TYPE: other nucleic acid
            ( A ) DESCRIPTION: /desc = "oligonucleotide"

( x i ) SEQUENCE DESCRIPTION: SEQ ID NO:9:

CGCGGCAGCC AC                                                                                       12

( 2 ) INFORMATION FOR SEQ ID NO:10:

( i ) SEQUENCE CHARACTERISTICS:
            ( A ) LENGTH: 13 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "oligonucleotide"

( x i ) SEQUENCE DESCRIPTION: SEQ ID NO:10:

GCGGCAGCCA CAC                                                                                      13

( 2 ) INFORMATION FOR SEQ ID NO:11:

( i ) SEQUENCE CHARACTERISTICS:
            ( A ) LENGTH: 12 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "oligonucleotide"

( x i ) SEQUENCE DESCRIPTION: SEQ ID NO:11:

CACCGACGGC GC                                                                                       12

( 2 ) INFORMATION FOR SEQ ID NO:12:

( i ) SEQUENCE CHARACTERISTICS:
            ( A ) LENGTH: 13 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "oligonucleotide"

( x i ) SEQUENCE DESCRIPTION: SEQ ID NO:12:

CACACCGACG GCG                                                                                      13

( 2 ) INFORMATION FOR SEQ ID NO:13:

( i ) SEQUENCE CHARACTERISTICS:
            ( A ) LENGTH: 12 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "oligonucleotide"

( x i ) SEQUENCE DESCRIPTION: SEQ ID NO:13:

CGCGGCCGCC AC                                                                                       12

( 2 ) INFORMATION FOR SEQ ID NO:14:

( i ) SEQUENCE CHARACTERISTICS:
            ( A ) LENGTH: 12 base pairs

-continued

```
       ( B ) TYPE: nucleic acid
       ( C ) STRANDEDNESS: single
       ( D ) TOPOLOGY: linear ( i i ) MOLECULE TYPE: other nucleic acid
       ( A ) DESCRIPTION: /desc = "oligonucleotide"

( x i ) SEQUENCE DESCRIPTION: SEQ ID NO:14:

C G C C G G A G C C   A C                                                   1 2

( 2 ) INFORMATION FOR SEQ ID NO:15:

( i ) SEQUENCE CHARACTERISTICS:
       ( A ) LENGTH: 16 base pairs
       ( B ) TYPE: nucleic acid
       ( C ) STRANDEDNESS: single
       ( D ) TOPOLOGY: linear ( i i ) MOLECULE TYPE: other nucleic acid
       ( A ) DESCRIPTION: /desc = "oligonucleotide"

( x i ) SEQUENCE DESCRIPTION: SEQ ID NO:15:

T T T T T T T T T   T T T T T                                               1 6

( 2 ) INFORMATION FOR SEQ ID NO:16:

( i ) SEQUENCE CHARACTERISTICS:
       ( A ) LENGTH: 4 amino acids
       ( B ) TYPE: amino acid
       ( C ) STRANDEDNESS:
       ( D ) TOPOLOGY: linear ( i i ) MOLECULE TYPE: peptide ( i x ) FEATURE:
       ( A ) NAME/KEY: Region
       ( B ) LOCATION: 1..4
       ( D ) OTHER INFORMATION: /note= "the sequence is repeated
              four or more times"

( x i ) SEQUENCE DESCRIPTION: SEQ ID NO:16:

Pro  Lys  Lys  Leu
     1
```